United States Patent
Lizardi et al.

(10) Patent No.: US 6,932,834 B2
(45) Date of Patent: Aug. 23, 2005

(54) SUTURE ANCHOR

(75) Inventors: José E. Lizardi, Franklin, MA (US); Jonathan Emerson Howe, Mansfield, MA (US); Gary McAlister, Franklin, MA (US); Kenneth L. Jensen, Providence, UT (US); Daniel A. Perkins, Hyde Park, UT (US)

(73) Assignee: Ethicon, Inc., Somerville, NJ (US)

( * ) Notice: Subject to any disclaimer, the term of this patent is extended or adjusted under 35 U.S.C. 154(b) by 504 days.

(21) Appl. No.: 10/183,697

(22) Filed: Jun. 27, 2002

(65) Prior Publication Data

US 2004/0002735 A1 Jan. 1, 2004

(51) Int. Cl.⁷ .............................................. A61B 17/04
(52) U.S. Cl. ........................ 606/232; 606/72; 606/228
(58) Field of Search ........................... 606/53, 60, 72, 606/73, 75, 86, 139–148, 219–233

(56) References Cited

U.S. PATENT DOCUMENTS

| 5,176,682 A | | 1/1993 | Chow |
| 5,207,679 A | * | 5/1993 | Li .............................. 606/72 |
| 5,522,845 A | * | 6/1996 | Wenstrom, Jr. ............. 606/232 |
| 5,527,342 A | | 6/1996 | Pietrzak et al. |
| 5,571,104 A | * | 11/1996 | Li .............................. 606/72 |
| 5,643,321 A | | 7/1997 | McDevitt |
| 5,662,654 A | * | 9/1997 | Thompson .................... 606/72 |
| 5,849,004 A | * | 12/1998 | Bramlet ...................... 606/232 |
| RE36,289 E | | 8/1999 | Le et al. |
| 5,935,129 A | | 8/1999 | McDevitt et al. |
| 6,007,566 A | * | 12/1999 | Wenstrom, Jr. ............. 606/232 |
| 6,022,373 A | | 2/2000 | Li |
| 6,287,324 B1 | | 9/2001 | Yarnitsky et al. |
| 6,319,269 B1 | | 11/2001 | Li |
| 2001/0000186 A1 | | 4/2001 | Bramlet et al. |

FOREIGN PATENT DOCUMENTS

WO  WO01 95809 A  12/2001

OTHER PUBLICATIONS

EPO Search Report dated Oct. 13, 2003 for EPO Appln. No. EP 03 25 4049.
Harpoon® Suture Anchors, Arthrotex® A Biomet Company, (Brochure).
Ultrafix® Micromite™ Small Joint Suture Anchor, Linvatec, a Subsidiary of ConMed Corporation, (Brochure).

* cited by examiner

*Primary Examiner*—Glenn K. Dawson
(74) *Attorney, Agent, or Firm*—Emil Richard Skula

(57) ABSTRACT

A suture anchor for affixing soft tissue to bone. The anchor has a hollow outer member, and an actuation member slidably mounted within the outer member. The actuation member has at least two engagement members that are pivotally mounted to the actuation member. Proximal movement of the actuation member with respect to the outer member causes the engagement members to move outward to a deployed position, wherein the engagement members are deployed in bone. A surgical suture is mounted to the anchor.

23 Claims, 18 Drawing Sheets

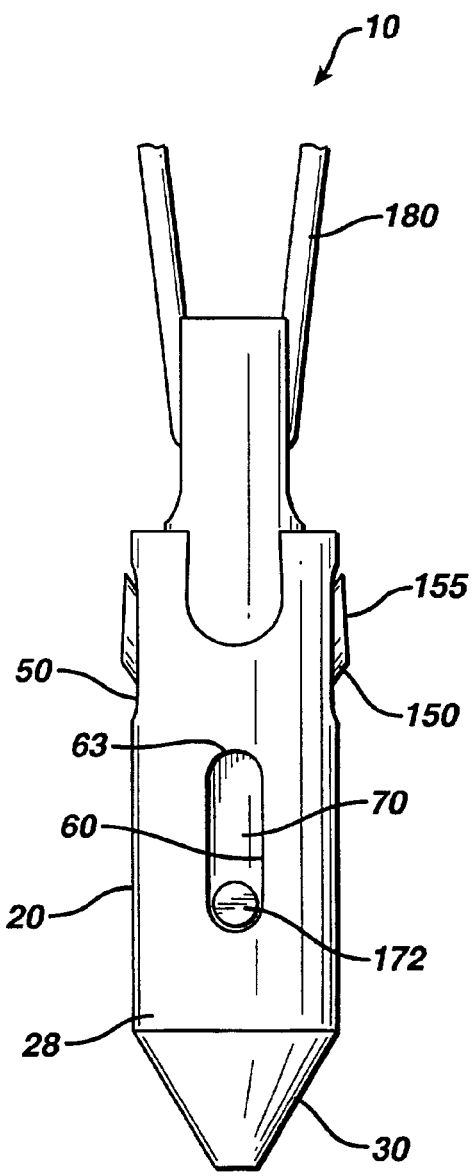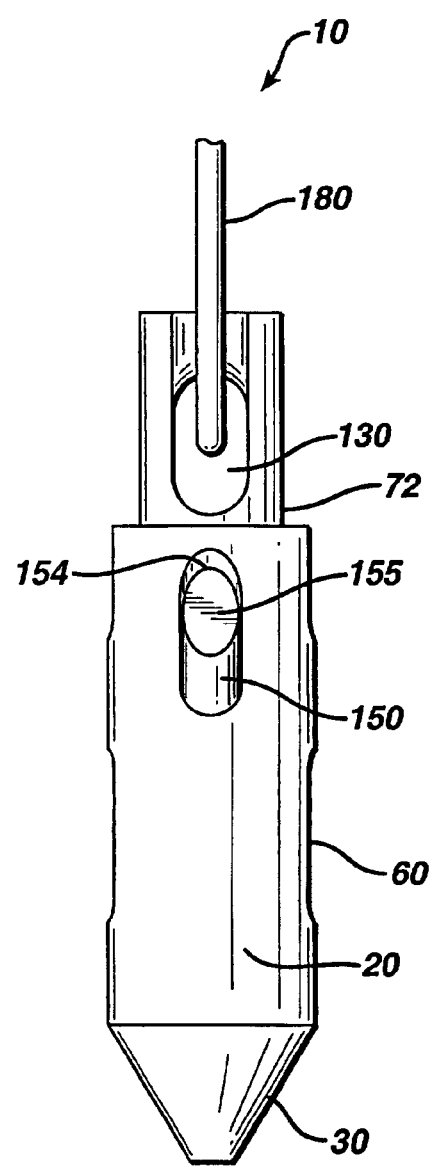
FIG. 10  FIG. 11

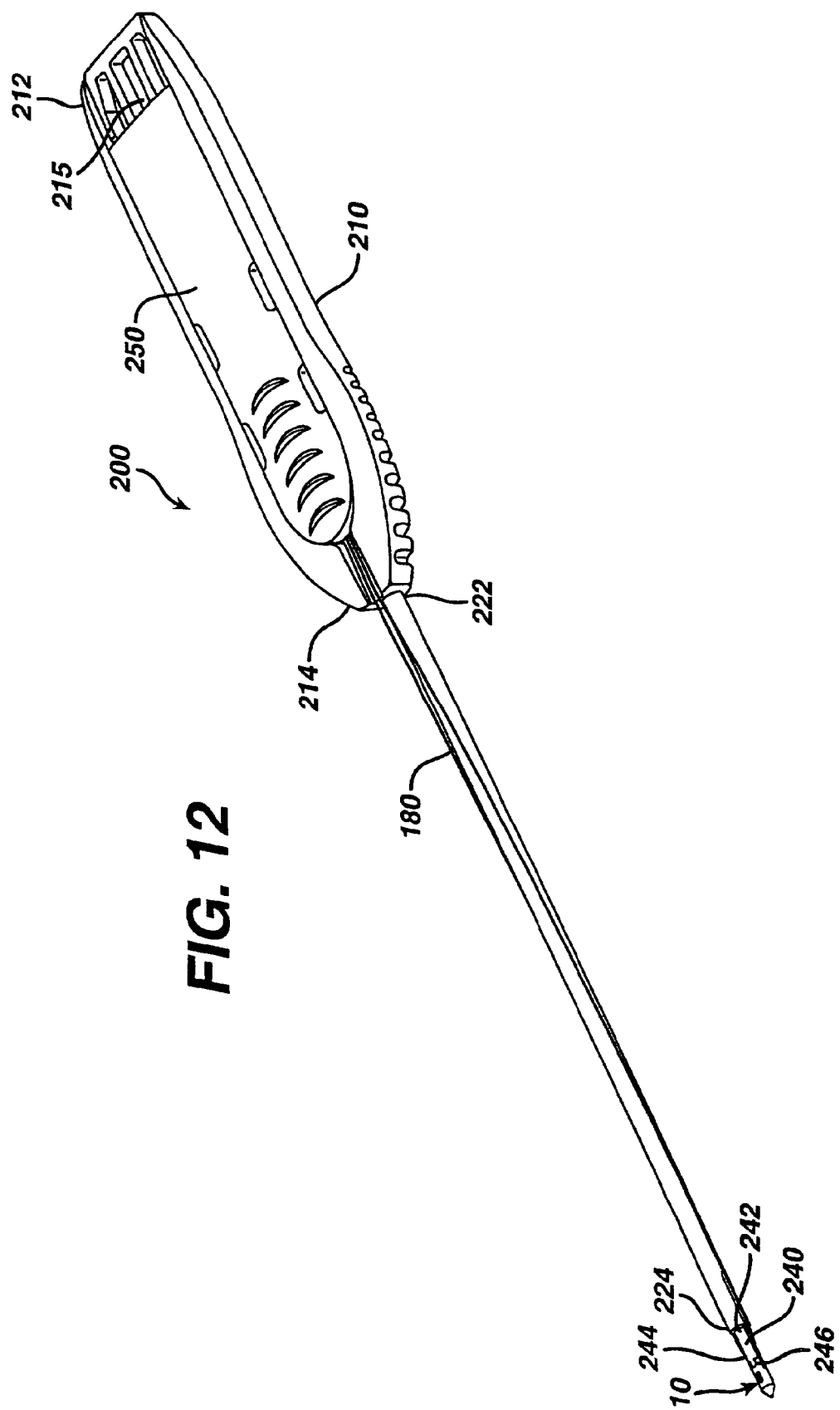

SUTURE ANCHOR

TECHNICAL FIELD

The field of art to which this invention pertains is medical devices and surgical procedures for repairing soft tissue injuries, more specifically, suture anchors and methods of using these suture anchors to affix soft tissue to bone.

BACKGROUND OF THE INVENTION

Suture anchor devices are known in the art of arthroscopy and orthopedic surgery for use in repairing soft tissue injuries in joints. A joint, such as the knee, the elbow, or the shoulder, contains tissue such as ligaments, tendons and cartilage, which allows the joint to function. For example, the soft tissue permits joint articulation, and the transmission and absorption of forces. Frequently, as a result of trauma caused by an accident or overloading of a joint during sports activities, the soft tissue may become damaged. It is not unusual in a sports related injury to have tearing of cartilage or the separation of a tendon or ligament from a bone surface. Such injuries tend to result in loss of joint function to a greater or lesser degree, and typically require some sort of surgical intervention and remediation to provide normal joint function.

It is typical in this art to repair soft tissue injuries using medical devices that are commonly known as suture anchors. A suture anchor typically consists of an implantable member that engages bone and a suture mounted to the implantable member, for example, through an eyelet.

The suture anchors are typically employed in a surgical procedure in the following manner. The surgeon, after surgically accessing the damaged joint, drills a bore hole, typically a blind hole, into a bone adjacent to the joint where the soft tissue injury has occurred.

Then the surgeon inserts the suture anchor into the drilled hole and manipulates the anchor to assure engagement therein, such that the anchor is stationary in the hole. Next the surgeon passes the suture through the soft tissue, typically by using a surgical needle attached to the suture, and approximates the soft tissue against the surface of the bone, thereby completing the reattachment of the soft tissue. After such a surgical repair, the body's healing response will cause a natural healing and re-attachment of the soft tissue to the bone surface, and the damaged joint will typically regain normal function.

Although there are numerous suture anchors known in this art for soft tissue re-attachment, there is a constant need for novel suture anchors having advantageous characteristics.

SUMMARY OF THE INVENTION

Therefore, it is an object of the present invention to provide a novel suture anchor, which is deployed by manipulation after insertion into a drilled hole in bone.

It is another object of the present invention to provide a suture anchor, which is deployable at a specific location within such a bone hole.

It is yet a further object of the present invention to provide a suture anchor that is removable from such a bone hole subsequent to deployment.

Accordingly, a suture anchor is disclosed. The suture anchor has outer member having a proximal end, a distal end, an inner cavity, an outer surface, and an inner surface. An optional distal nose member extends from the distal end of the outer member. There is an opening in the proximal end of the outer member in communication with the inner cavity. A pair of engagement member slots in the outer member extends through the outer surface. The slots are in communication with the inner cavity, and each slot has a proximal end and a distal end. The anchor has an actuation member slidably mounted in the cavity of the outer member. The actuation member has a proximal end, a distal end, and an outer surface. There is a cavity in the actuation member. A pivot pin is mounted in the cavity of the actuation member. The pin member has opposed ends and an outer surface. A pair of engagement members is pivotally mounted in the cavity of the engagement member about the pivot pin. Each engagement member has a proximal end, a distal end, and an outer surface. There is a camming surface that extends distally into the cavity of the actuation member. The actuation member is moveable from a first distal position wherein the engagement members are substantially contained within the outer member to a second proximal position wherein at least the proximal ends of the engagement members extend out through the slots of the outer member such that said engagement members may engage bone.

Still yet another aspect of the present invention is a method of affixing soft tissue to bone utilizing the suture anchors of the present invention, such as that described above. An anchor of the present invention is deployed in a bore hole drilled in bone and the anchor is deployed in a position within the bone bore hole such that the engagement members are deployed in bone surrounding the bone bore hole. Sutures mounted to the suture anchor are then used to affix soft tissue to a surface of the bone.

These and other aspects and advantages of the present invention will become more apparent from the following description and accompanying drawings.

BRIEF DESCRIPTION OF THE DRAWINGS

FIG. 10 is a side view of a suture anchor of the present invention in the undeployed configuration illustrating the end of the pin member in the pin slot, and the end of the engagement members contained within the engagement member slots.

FIG. 11 illustrates the anchor of FIG. 10 rotated 90° about the longitudinalaxis illustrating the engagement members protruding into the engagement member slots of the outer member.

FIG. 12 illustrates an anchor of the present invention mounted to an insertion tool.

DESCRIPTION OF THE PREFERRED EMBODIMENTS

Figure 1:
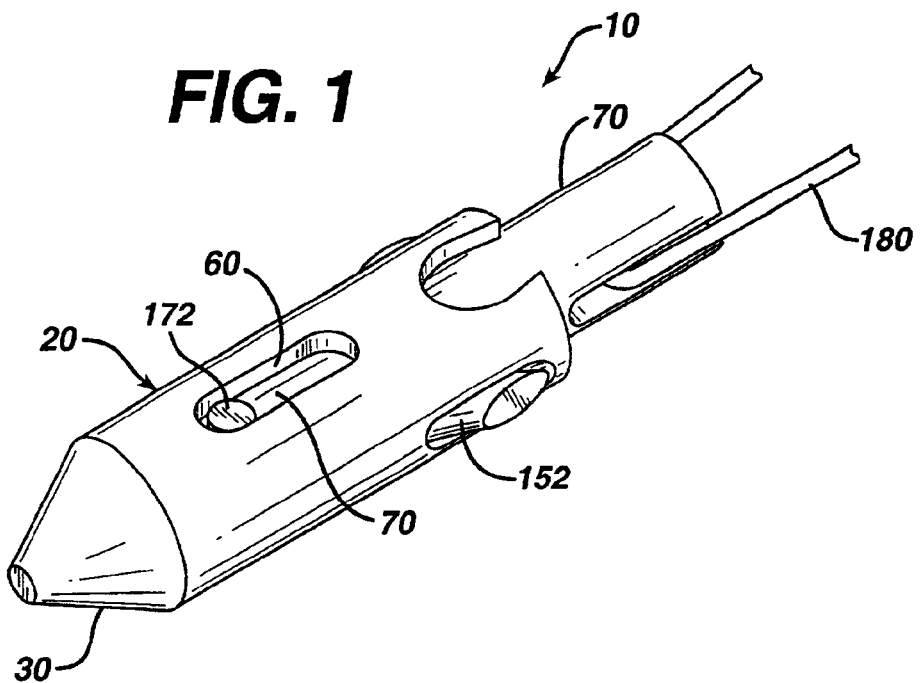
FIG. 1 is a perspective view of a preferred embodiment of a suture anchor of the present invention illustrated prior to deployment.
Figure 2:
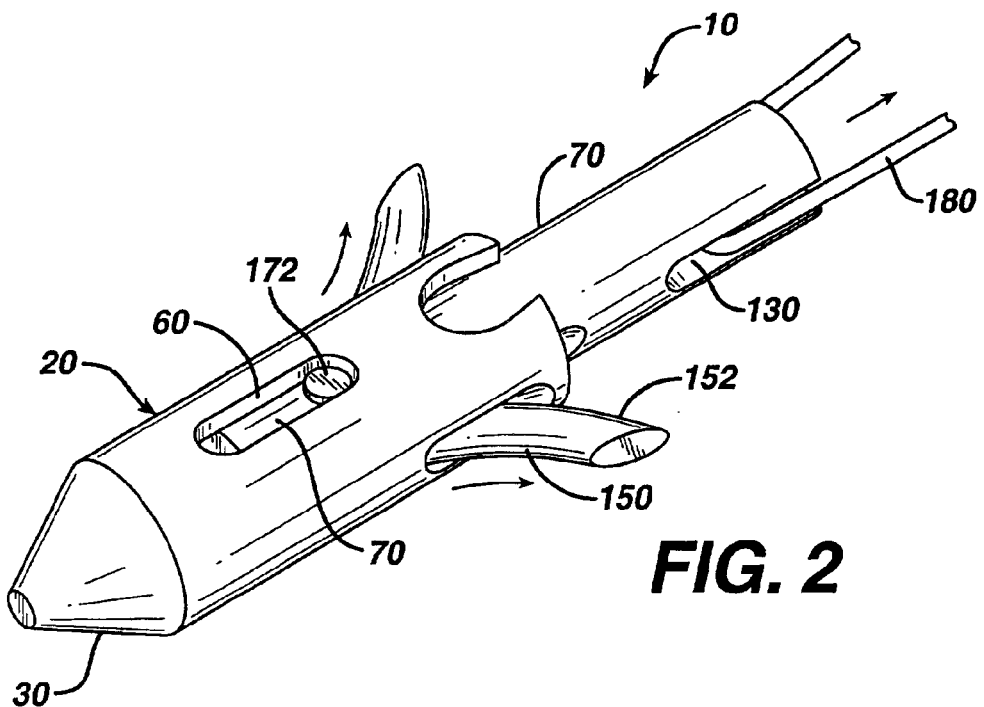
FIG. 2 is a perspective view of a suture anchor of FIG. 1 in a fully-deployed position wherein the engagement members are deployed outwardly.
Figure 3:
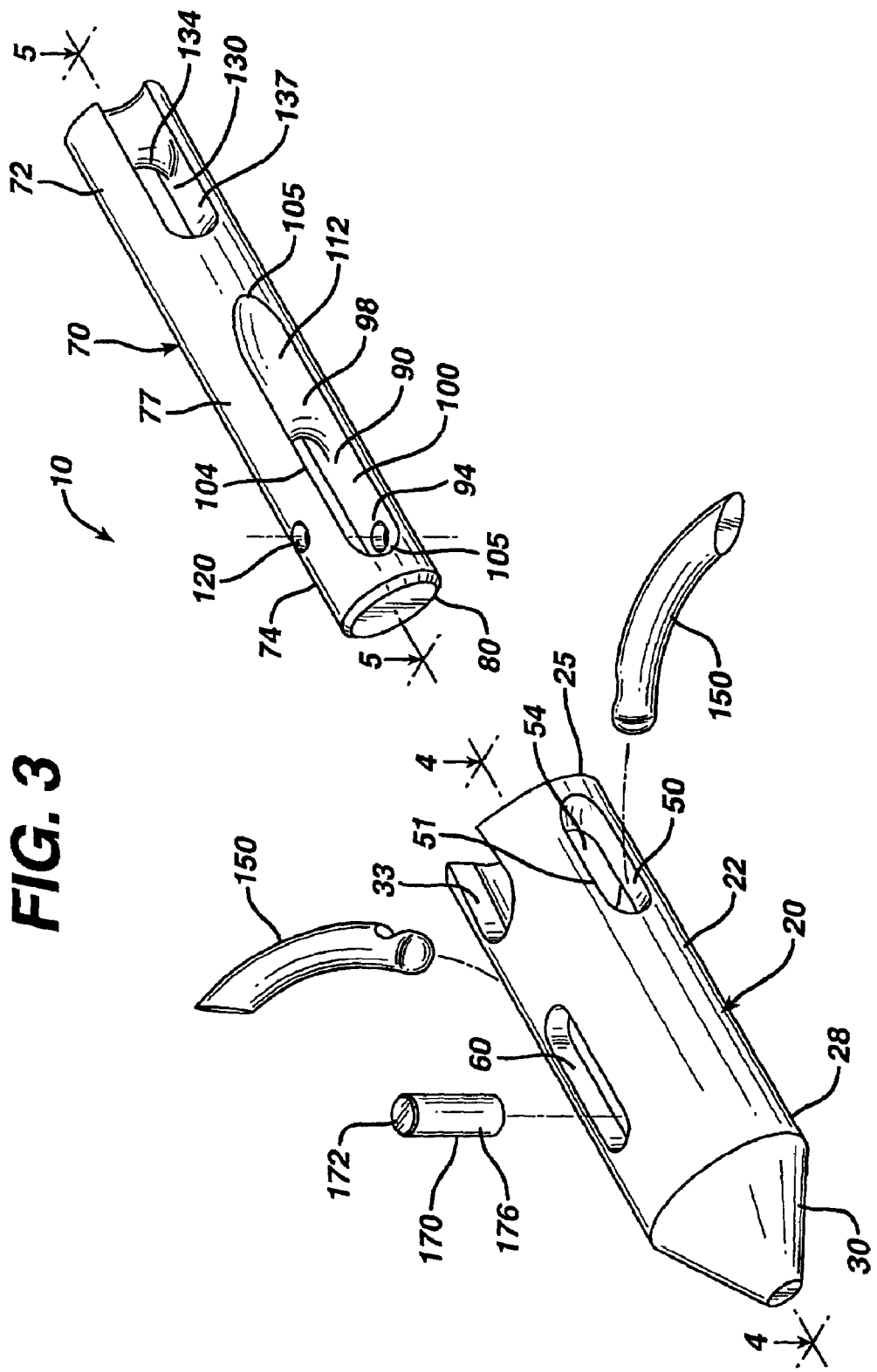
FIG. 3 is an exploded perspective view of the suture anchor of FIG. 1.
Figure 4:
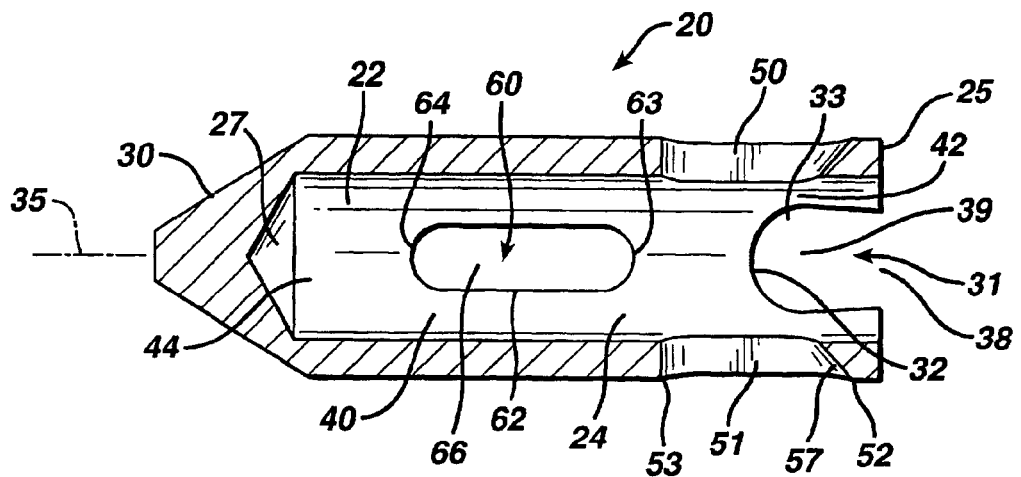
FIG. 4 is a cross-sectional view of the outer member of the anchor of FIG. 3 taken along view line 4—4.
Figure 5:
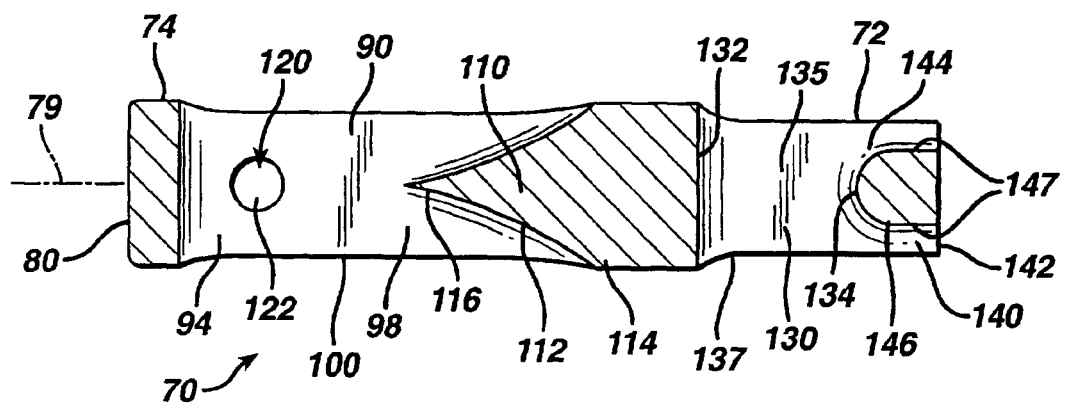
FIG. 5 is a cross-sectional view of the actuation member of FIG. 3 taken along view line 5—5.
Figure 6:
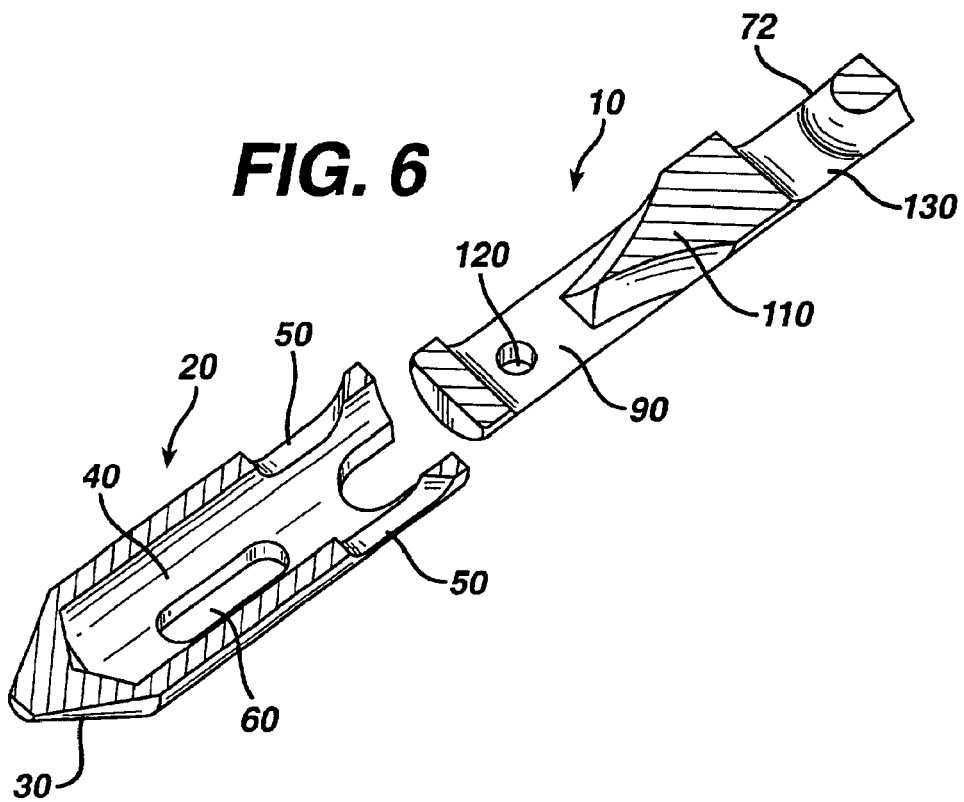
FIG. 6 is a perspective view of an outer member and an engagement member shown in cross-section, prior to assembly.
Figure 7:
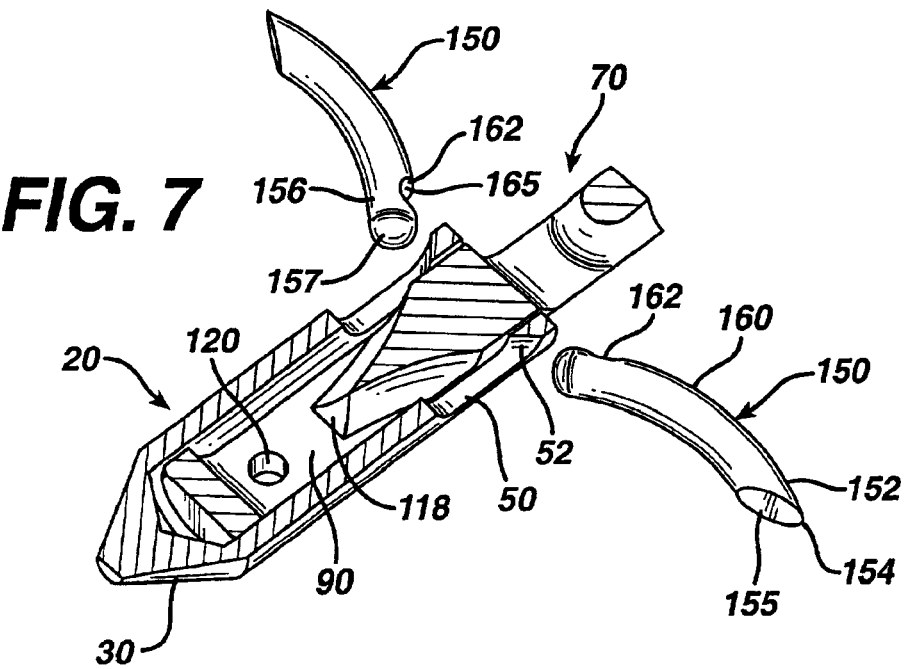
FIG. 7 is a perspective view of the outer member and the actuation member of FIG. 6, illustrating the actuation member inserted into the outer member, and also illustrating the engagement members prior to assembly.
Figure 8:
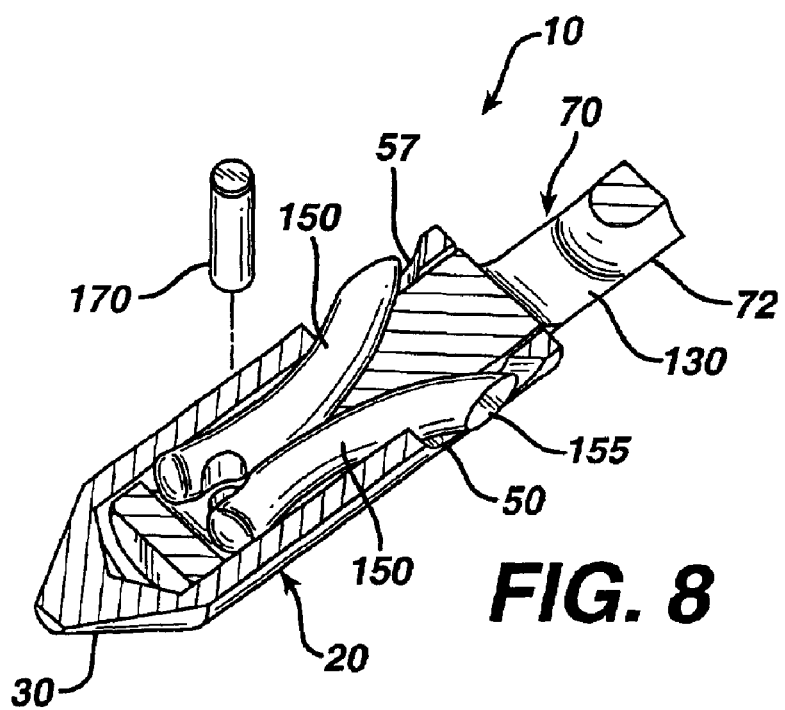
FIG. 8 is a cross-sectional perspective view illustrating the assembly of the engagement members into the cavity of the actuation member of FIG. 7, and also illustrating the pin member.
Figure 9:
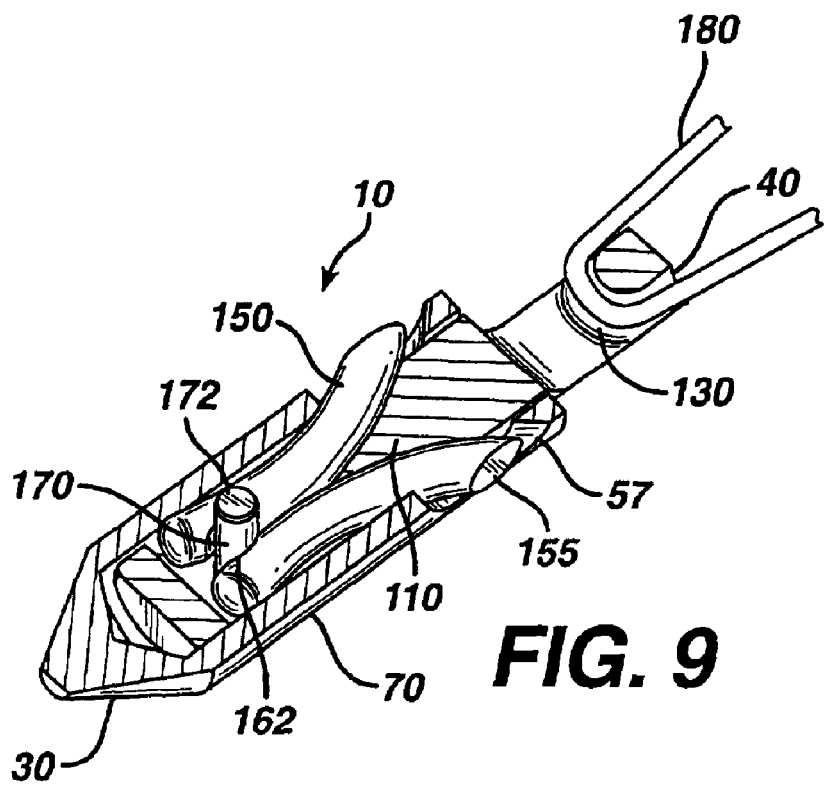
FIG. 9 illustrates a cross-sectional perspective view of the suture anchor of FIG. 8 fully assembled with the pin emplaced and a suture mounted to the anchor.

The suture anchors of the present invention are made from conventional biocompatible materials known in this art and equivalents thereof. The biocompatible materials may be absorbable or non-absorbable. Examples of biocompatible, non-absorbable materials include metals such as titanium, surgical stainless steel, Nitinol, and the like and combinations thereof, equivalents thereof and the like. The biocompatible non-absorbable materials may include conventional ceramics such as alumina, equivalents thereof and the like. The anchors of the present invention may also be made from conventional nonabsorbable composite materials and the like.

The biocompatible bioabsorbable and bioresorbable materials that can be used to manufacture the suture anchors of the present invention include conventional, known bioabsorbable and bioresorbable polymers including tricalcium phosphate, polylactic acid, polyglycolic acid and the like and equivalents thereof and combinations thereof. If desired, the suture anchors of the present invention may be made from both bioabsorbable and non-absorbable components. In a preferred embodiment, surgical sutures are mounted to the one or more of the ends of the sutures.

The sutures useful for mounting to the suture anchors of the present invention will be conventional surgical sutures made from conventional biocompatible materials. The materials may be absorbable or nonabsorbable, and natural or synthetic. Absorbable materials include polylactic acid, polydioxanone, equivalents thereof and the like. Nonabsorbable materials include polyester and the like. The sutures may be braided or monofilament.

The suture anchors of the present invention are manufactured in a conventional manner using conventional manufacturing techniques such as machining, casting, molding, extruding and the like and equivalents thereof. The manufacturing techniques employed will be dependent upon the materials of construction selected.

Referring now to FIGS. 1–4, a suture anchor 10 of the present invention is seen. Anchor 10 is seen to have outer member 20. Outer member 20 is seen to be a hollow elongated member having a proximal end 25 and a distal end 28. Extending distally from distal end 28 is the nose member 30 having a substantially conical configuration. If desired nose member 30 may have other geometric configurations including arcuate, flat, bullet-shaped, spade-shaped, curved, semicircular, flat, pyramidal, etc., and combinations thereof. Member 20 is seen to have a rod-like shape having a preferred circular cross-section. If desired, member 20 may have other cross-sections including elliptical, polygonal, square, rectangular, triangular, and combinations thereof. Member 20 is seen to have outer surface 22, inner surface 24 and longitudinal axis 35. The member 20 has inner cavity 40 having proximal end 42 and distal end 44. Proximal end 42 of cavity 40 is in communication with the opening 38 in proximal end 25. Distal end 44 of cavity 40 is adjacent to and bounded by distal section 27 of inner surface 24. Member 20 is also seen to have side slots 50 having openings 54 that extend through member 20 and are in communication with inner cavity 40. Slots 50 are seen to have opposed sides 51, distal end 53 and proximal end 52. Extending distally from proximal end 52 is the camming surface 57. Also extending through the side wall of member 20 are the opposed pin slots 60. Pin slots 60 are seen to have sides 62, and proximal end 63 and distal end 64. Opposed ends 63 and 64 are preferably curved or arcuate, but may be squared off or have other geometric configurations. Pin slots 60 are seen to have openings 66 in communication with inner cavity 40. The optional instrument receiving slots 31 are seen to be contained in either side of the proximal end 25 of member 20. The opposed key receiving slots 31 are seen to have bottoms 32, sides 33, and side openings 39 and top openings 38. Openings 39 extend through and are in communication with proximal section 42 of cavity 40.

Anchor 10 is also seen to have actuation member 70. Actuation member 70 is seen to be a rod-like member having a proximal end 72, a distal end 74, an outer surface 77 and a longitudinal axis 79. Actuation member 70 preferably has a circular cross-section, but may if desired have other geometric cross-sections including elliptical, polygonal, rectangular, triangular, square, and combinations thereof. Distal end 74 is seen to preferably have a substantially flat end surface 80, but may have other configurations as well including for example arcuate or rounded, conical, pyramidal, etc. Actuation member 70 is seen to have engagement member receiving cavity 90 for receiving and mounting engagement members 150. The cavity 90 is seen to have distal section 94 and proximal section 98. The cavity 90 is seen to communicate with opposed lateral openings 100. Lateral openings 100 are seen to have an elongated shape, and further have opposed sides 104 and opposed rounded ends 105. Ends 105 are preferably rounded but may have other geometric configurations. Extending distally into the proximal section 98 of cavity 90 is the camming member 110 having camming surfaces 112. Camming surfaces 112 are seen to have proximal ends 114 and distal ends 116 that intersect to form distal surface 118. The camming surfaces 122 are seen to have a convex inward curve, but may have other configurations including for example parallel surfaces extending to distal ends 116. The member 70 is also seen to have a pair of opposed pin hole openings 120 having passages 122 that extend inward from outer surface 77, such that passages 122 are in communication with cavity 90. The openings 120 are seen to be circular in shape, but may have other configurations including square, elliptical, polygonal, rectangular, etc., combinations thereof and the like.

The suture mounting opening 130 is seen to extend transversely through member 70 adjacent to the proximal end 74. Suture mounting opening 130 is seen to have bottom 132, top 134, passage 135 and opposed openings 137 in communication with passage 135. Optionally, although not illustrated in the drawings, suture mounting opening can be replaced with other conventional suture mounting members such as a conventional eyelet extending proximally from proximal end 72 of member 70 or from the proximal end of member 20, a suture loop mounted to the member 70 or the member 20, etc. The suture containment slots 140 are seen to extend distally from proximal end 74 through to opening 130. The slots 140 are seen to extend radially into member 70 through outer surface 77. The slots 140 are seen to have proximate open ends 142, distal ends 144, opening 145 and inner surface 146 having bottom 147. Mounted to anchor 10 is a suture 160 that is partially contained in slots 140 and extends through suture mounting opening 130. A suture 180 is seen to pass through mounting opening 130 and to be partially contained within slots 140.

Mounted in the cavity 90 of actuation member 70 are the engagement members 150. Engagement members 150 are seen to be rod-like members having an arcuate shape. Although not preferred, the members 150 may be tubular in nature having inner longitudinal passages or lumens. In addition, although it is preferred that the engagement members 150 have a curved or arcuate configuration, the engagement members 150 may have other configurations including straight, combinations of straight and arcuate sections, curved, parabolic, semi-circular, combinations thereof and the like. The engagement members 150 are seen to have proximal ends 152, distal ends 156 and outer surfaces 160.

Proximal ends 152 are seen to be angulated in order to form piercing edges 154. Proximal ends 152 are seen to have flat endfaces 155. However, if desired, proximal ends 152 may be configured to be blunt, rounded, pointed, etc. Distal ends 156 are seen to have rounded end faces 157, but endfaces 157 may have other configurations such as flat, etc. Each engagement member 150 is seen to have camming indentation 162 extending into the member 150 adjacent to distal end 156. The indentations 162 are seen to have camming surfaces 165. Also mounted in member 70 is the pin member 170. Pin member 170 is seen to be an elongated cylindrically shaped pin having opposed ends 172 and outer surface 176. Pin member 170 is seen to extend through the passages 122 of pin hole openings 120 and into cavity 90 at distal end section 94. The outer surface 176 of pin member 170 is seen to engage camming surfaces 165 of engagement members 150.

The engagement members 150 are mounted in cavity 94 of member 90 such that the camming indentations 162 are adjacent to pin 170, and surfaces 165 engage outer surface 176. Actuation member 70 is slidably mounted in cavity 40 of outer member 20 such that the actuation member is movable longitudinally from a first distal position wherein the engagement members 150 are not deployed to a second proximal position wherein the engagement members 150 are deployed radially outwardly through slots 50 of member 20. The ends of pin member 170 are slidable within slots 60. The width of slots 60 is sufficient to provide for effective sliding motion of pin ends 172. Optionally, the width of slot 60 may be such that an interference or friction fit is provided between the sides 62 of slot 60 and the surface 176 of pin member 170 at pin ends 172. This will result in an increased force being required to proximally move the actuation member 70 in order to deploy the engagement members. This increased force required to move the actuation member 70 may provide the user with improved control of the deployment of the anchor 10 and deter or prevent inadvertent deployment.

The suture anchors 10 of the present manner operate mechanically in the following manner. Prior to deployment, the actuation member 70 is located in an initial distal position within cavity 40 of outer member 20. The engagement members are substantially contained with cavity 90 of actuation member 70, with the proximal ends 152 of engagement members 150 extending into and contained within the slots 50 of outer member 20. If desired, engagement member 150 can be completely contained within cavity 90 prior to deployment and not extend into slots 150. Pin ends 172 are seen to be contained 29 within in slots 160 in an initial distal position. If desired, although not preferred, pin ends 172 may extend out from slots 60 above the surface 22 of outer member 20. In order to deploy the anchor 10, and cause the engagement members 150 to be deployed into surrounding bone, a proximal force is exerted upon the actuation member 70, preferably by pulling proximally on a suture mounted to the actuation member 70 such as suture 180. The proximal force caused the member 70 to slide proximally in cavity 40, with outer surface 77 sliding against inner surface 24 of member 20. The proximal motion causes the outer surfaces 160 of engagement members 150 to contact camming surfaces 112 of member 70 and camming surfaces 57 of slots 150. As the actuation member 70 moves proximally, the pin ends 172 move proximally in slots 160. The camming surfaces 112 and 57 cause the engagement members 150 to pivot about pin 170 and rotate radially outwardly though and out of slots 50. The camming surface 165 of indentation 162 is in contact with and slides over outer surface 176 of pin 170 during employment. The engagement members are fully deployed when the proximal movement of the member 70 is stopped by pin ends 172 engaging the proximal end 63 of slot 60.

The suture anchors 10 are assembled in the following manner. Referring to FIGS. 6–9, initially the outer member 20 and the actuation member 70 are axially aligned. Then the actuation member 70 is inserted into cavity 40 of outer member 20, and displaced to a distal position. Next, the engagement members 130 are introduced through pin slots 60 on outer member 20 and into cavity 90 such that members 150 engage camming surfaces 122 on engaging member 70. The distal ends 156 are mounted such that the indentations 162 are proximate to the pin openings 120. Finally, the anchor assembly 10 is completed by introducing pin member 170 through slots 60 and into pin hole openings 120, such that the pin extends through outer member 20 and actuation member 70, and pin ends 172 are preferably contained within slots 60.

The size of the anchors 10 of the present invention will depend upon the surgical application and the individual characteristics of the patient and will be sufficient to effectively provide anchoring against a load. For example, the anchor dimensions will be larger for applications around a joint where the forces are expected to be larger such as 30 pounds, and smaller for applications where the anchor will be subjected to smaller forces such as 2 pounds. By way of example and not limitation, the diameters of the anchors can range from about 1.3 mm to about 5 mm, and the lengths of the anchors can range from about 4 mm to about 18 mm.

Referring now to FIG. 12., an insertion device 200 useful in inserting the suture anchors 10 of the present invention into bone bore holes is illustrated. The insertion device 200 is seen to have a handle 210 having a distal end 214 and a proximal end 212. Extending from the proximal end 212 of handle member 210 is the elongated member 220 having proximal end 222 and distal end 224. Member 220 is preferably a solid rod-like member having a lumen or passage therein, but may be a tubular member having a lumen. Although preferably having a circular cross-section, the member 220 may have other geometric cross-sections including elliptical, square, polygonal, rectangular, arcuate, combinations thereof and the like. Extending from the distal end 224 of member 220 is the mounting member 240. Mounting member 240 is seen to have proximal end 222 and distal end 244 having mounting key projections 246. The mounting member is preferably a rod-like member having a circular cross-section, but may have other cross-sections as described previously, and may be tubular. The anchor 10 is mounted to the distal end 244 of mounting member 240 by inserting the key projections 246 into key receiving slots 31 of outer member 20. Key receiving slots 31 provide a friction fit to retain key projections 246. Mounting member 240 is also seen to have suture containment slots 245 extending therein.

The proximal ends of the sutures 180 are retained by handle 210 within cavity 215, which is covered by slidably mounted cover member 250. In use, the cover member 250 can be slid proximally to uncover cavity 215, and suture 180 may then be withdrawn for use in the surgical procedure. Alternatively, the sutures 180 can be retained by a conventional retention member such as a hook, etc. on the outer surface of handle 210, and removed from engagement with the retention member for use.

Figure 13:
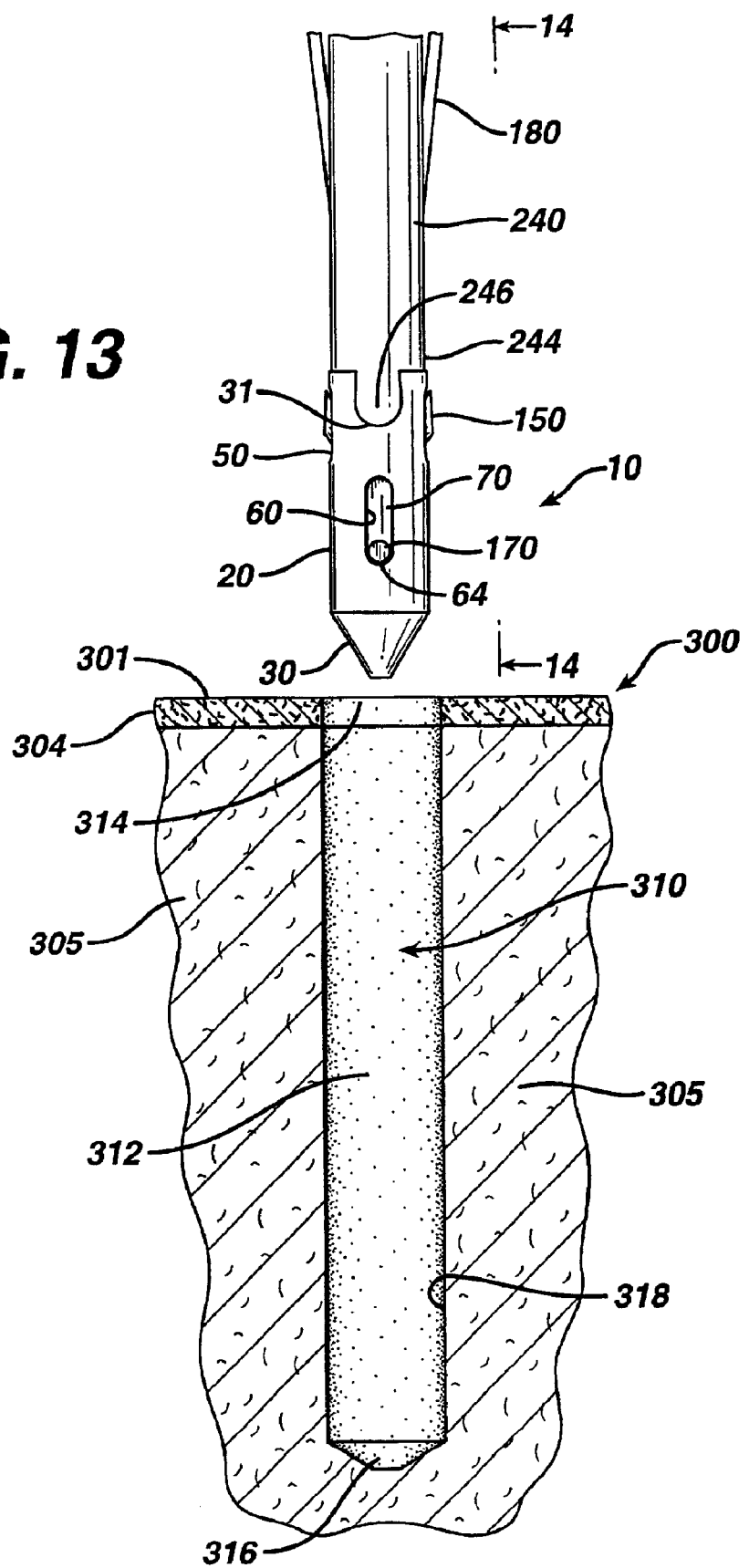
FIG. 13 illustrates an anchor of the present invention mounted to the distal end of an insertion tool immediately prior to insertion into a bone bore hole drilled in a bone adjacent to a joint.
Figure 14:
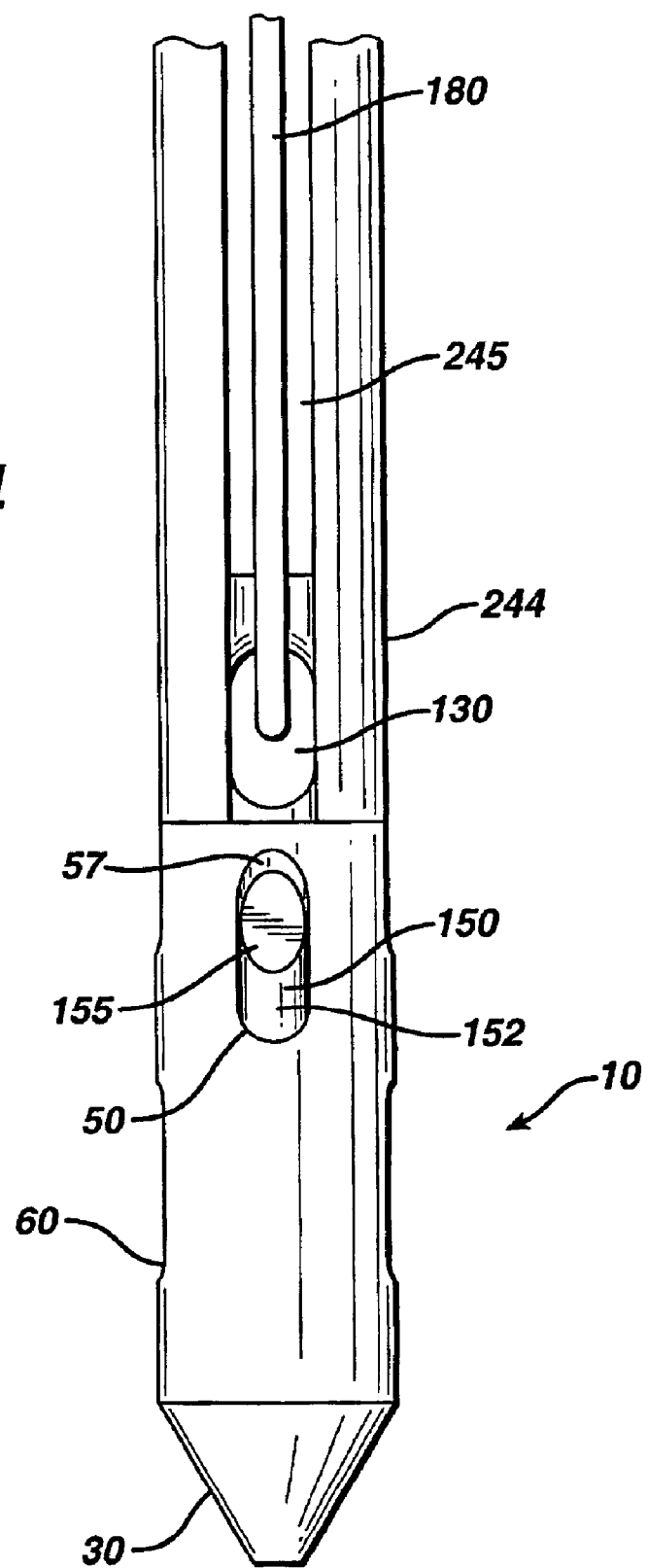
FIG. 14 is a magnified side view of the anchor and distal end of the insertion tool of FIG. 13 rotated 90° about the longitudinal axis to illustrate the suture and the arc engagement members prior to deployment.
Figure 15:
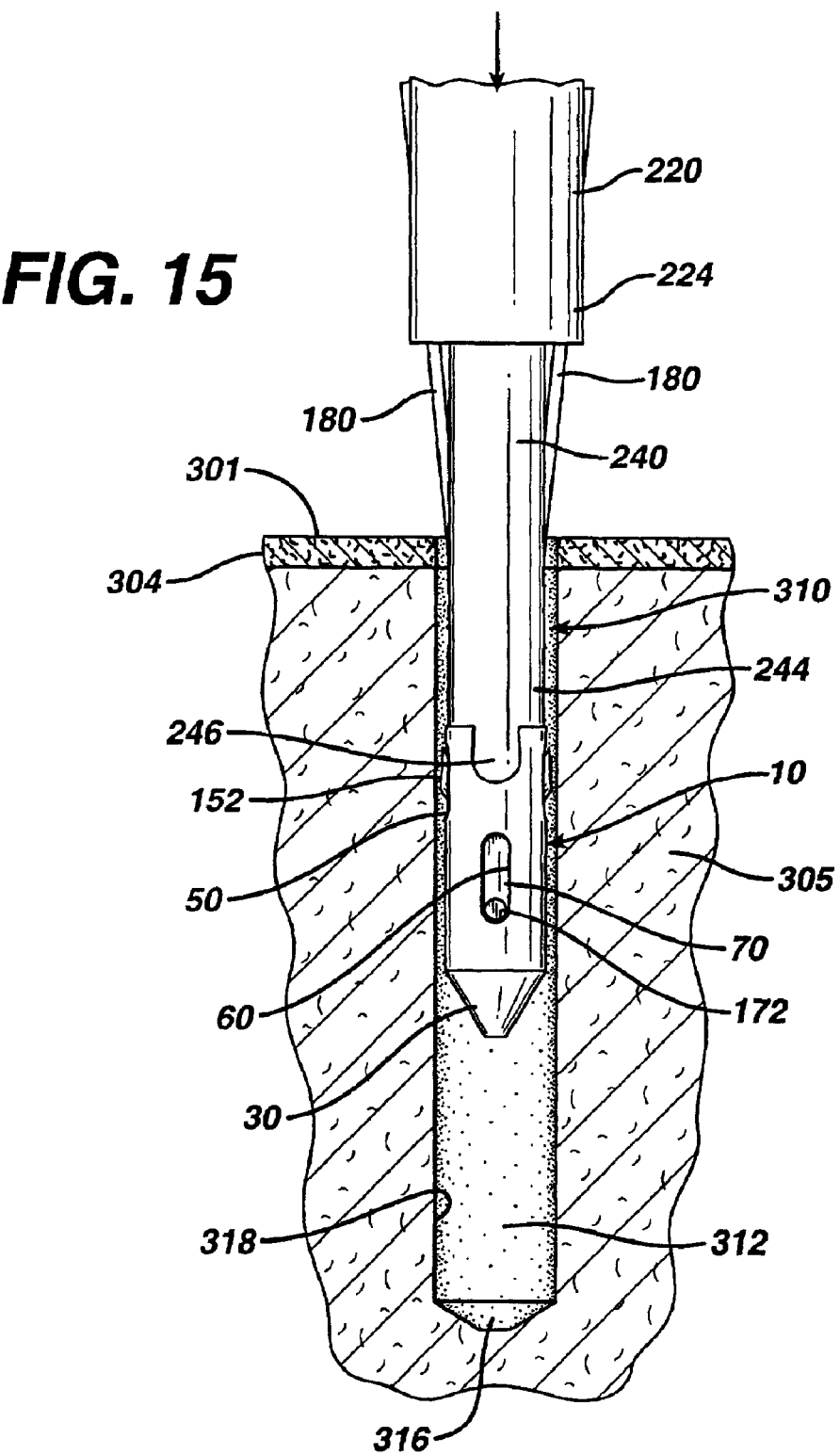
FIG. 15 illustrates the suture anchor partially inserted into the bone bore hole, with the anchor in the undeployed position.
Figure 16:
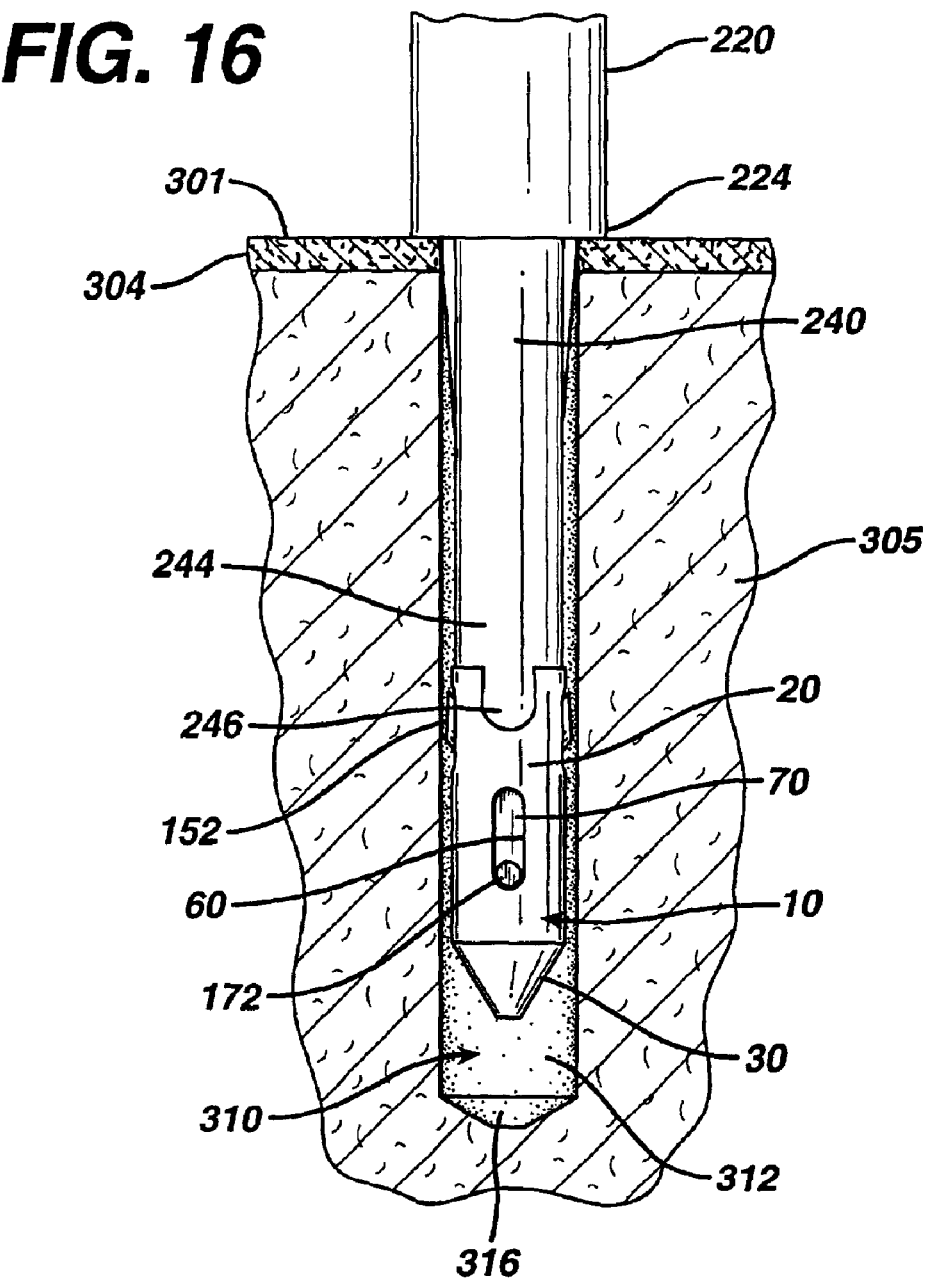
FIG. 16 illustrates the suture anchor emplaced in the bone bore hole at the desired deployment location prior to deployment of the anchor and the engagement members.
Figure 17:
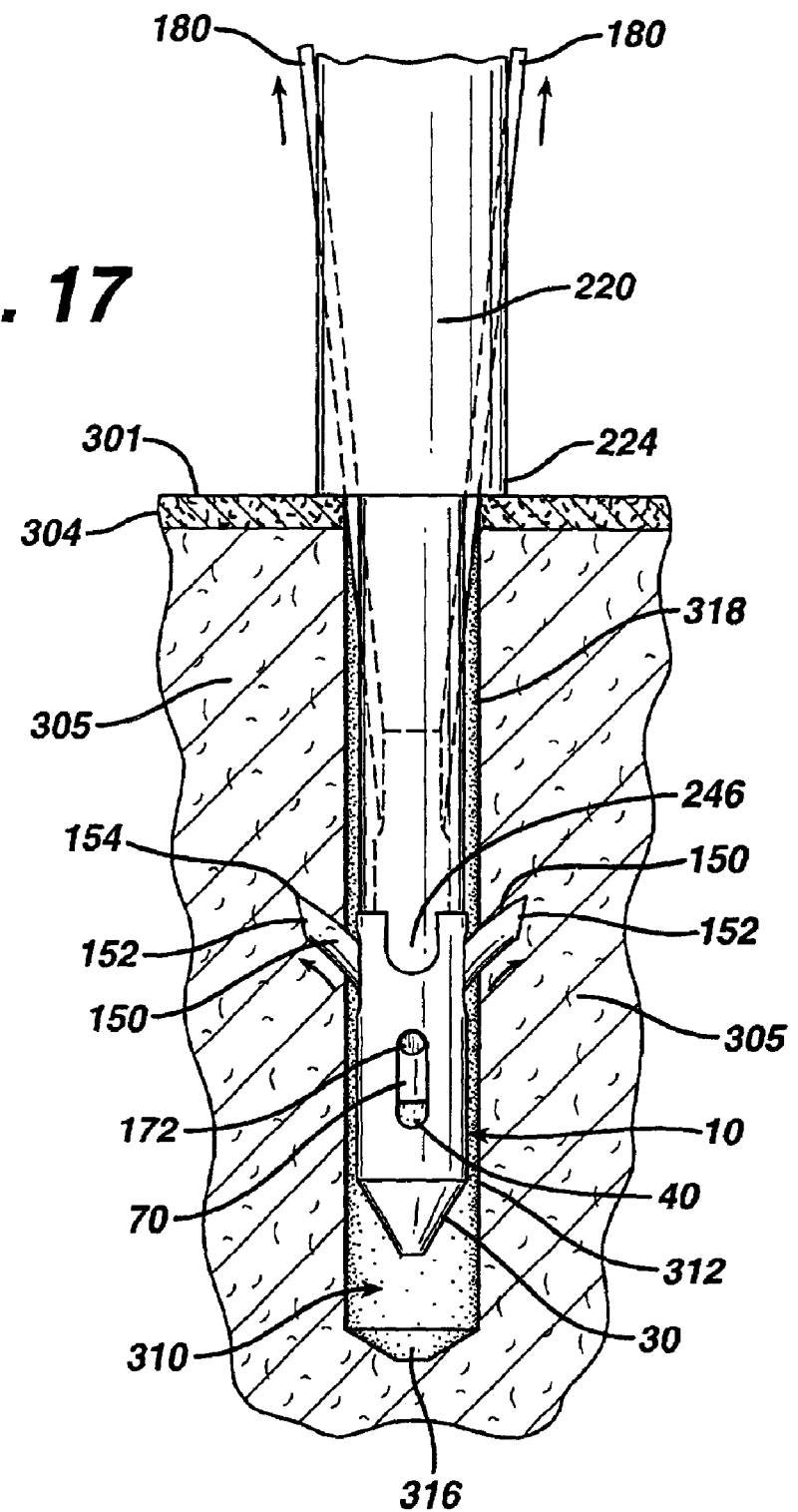
FIG. 17 illustrates the anchor of FIG. 16 with the anchor at the deployment location, with the anchor deployed and having the engagement members fully-deployed and engaged in bone surrounding the bore hole.
Figure 18:
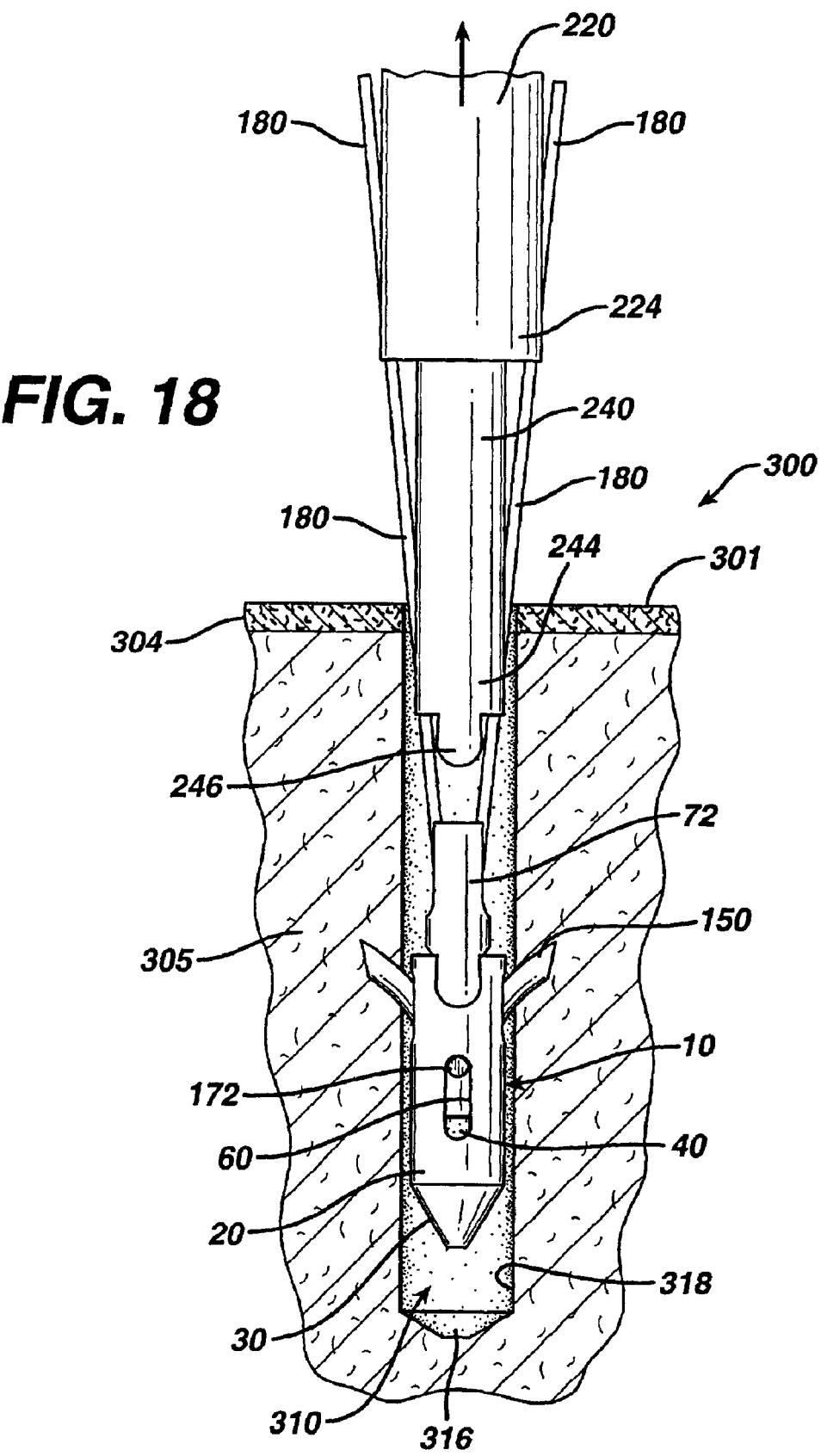
FIG. 18 illustrates the deployed anchor of FIG. 17, with the distal end of the insertion tool removed from the proximal end of the anchor.
Figure 19:
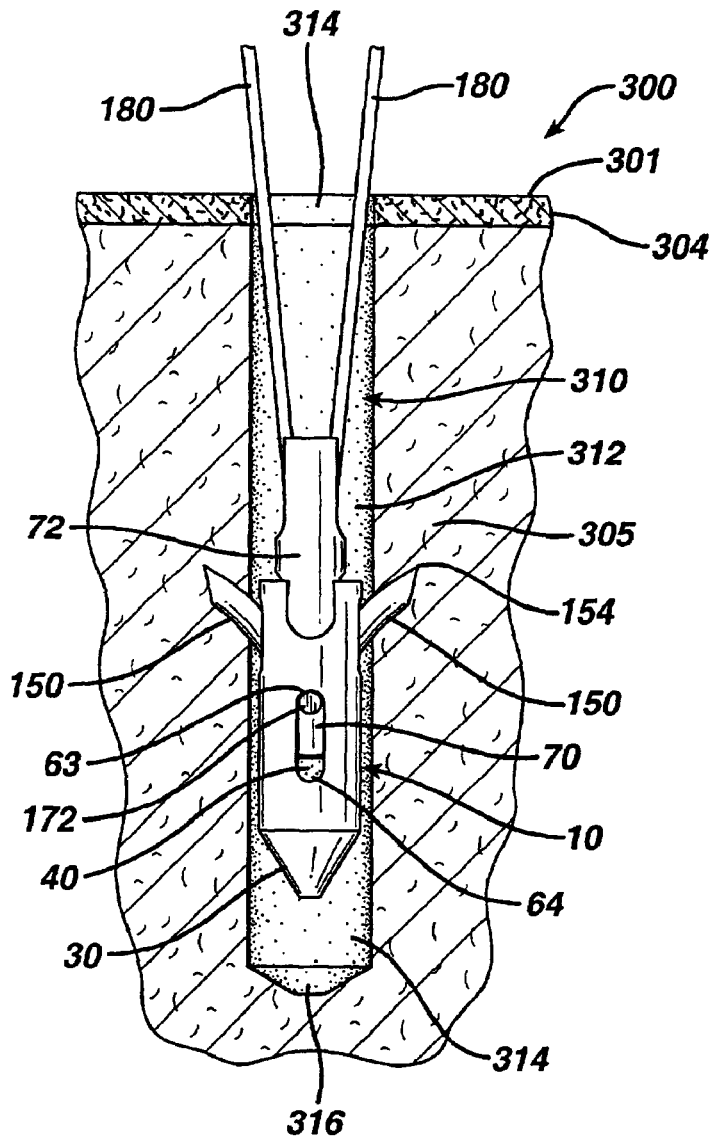
FIG. 19 illustrates the anchor deployed in the bore hole with the engagement members deployed in bone and having suture extending out from the bone bore hole, ready to mount or affix tissue to the surface of the bone.
Figure 20:
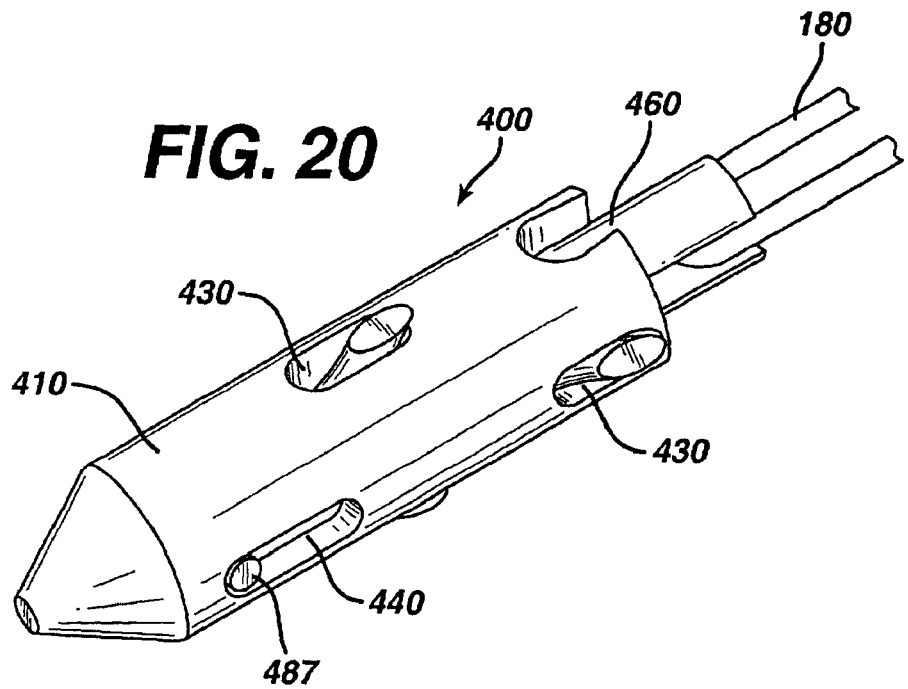
FIG. 20 is a perspective view illustrating an alternate embodiment of a suture anchor of the present invention having four engagement members; the anchor is in the undeployed position.
Figure 21:
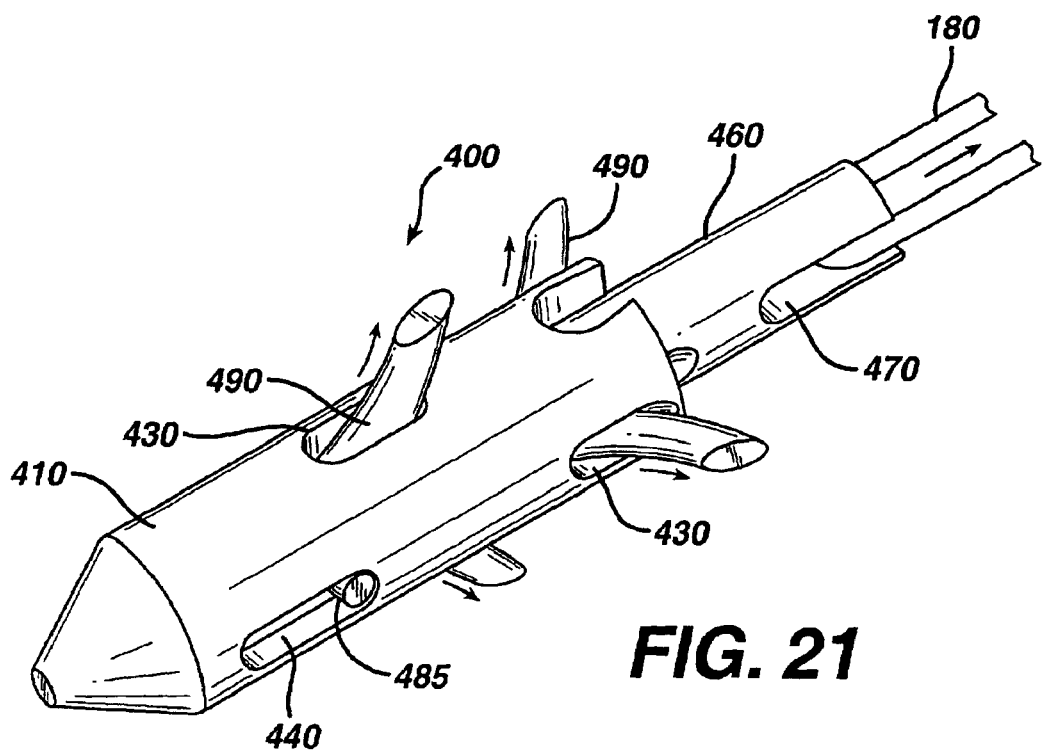
FIG. 21 is a perspective view of the anchor of FIG. 20 in the fully-deployed position wherein all four engagement members are fully rotated out of the engagement member slots.
Figure 22:
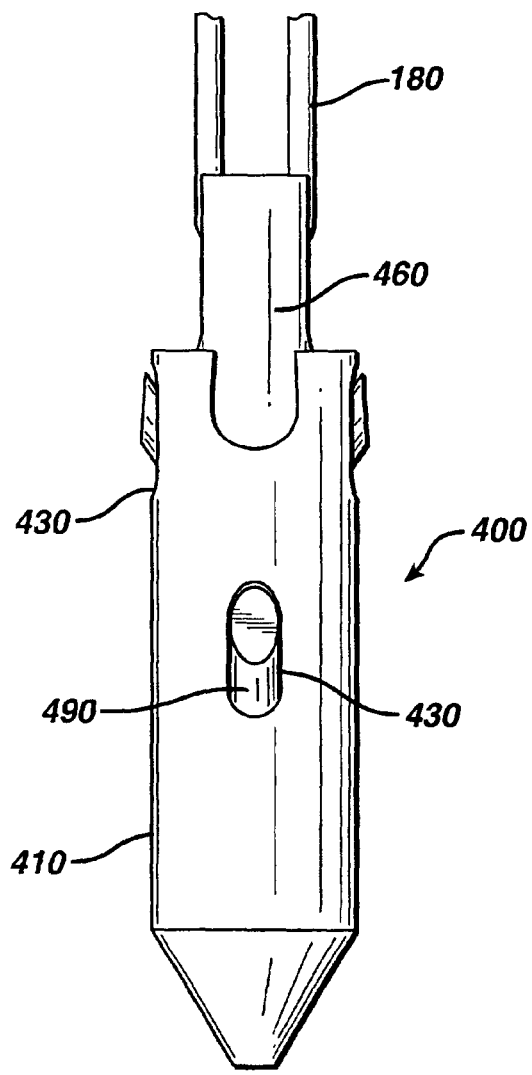
FIG. 22 is a side view of the anchor of FIG. 20.
Figure 23:
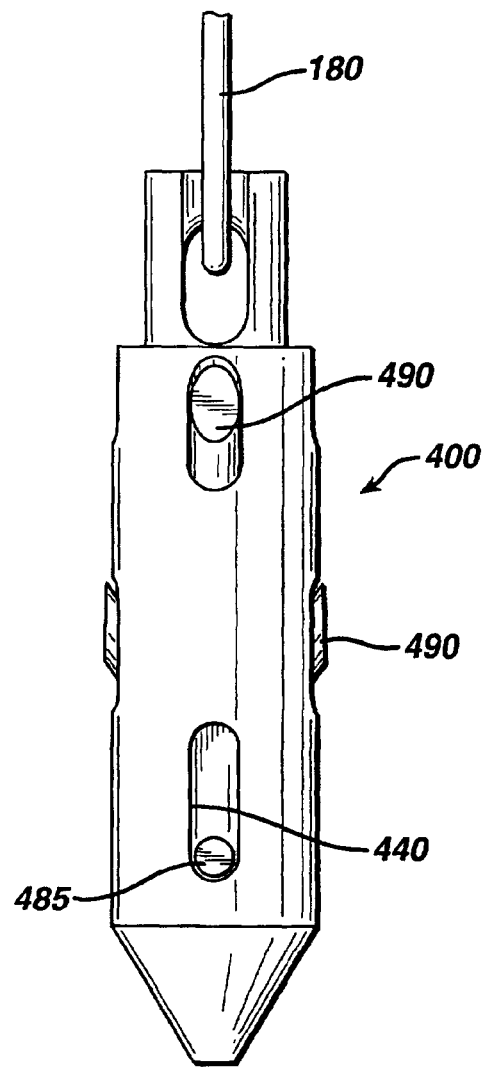
FIG. 23 is a side view of the anchor of FIG. 22 rotated 90 degrees about the longitudinal axis to illustrate the engagement members and the pin member and pin slot.

The use of the suture anchors 10 of the present invention is illustrated in FIGS. 13–19. As seen in FIG. 13, the anchor 10 mounted to instrument 200 (see FIG. 14) is located proximal to a bone 300. The anchor 10 is in the undeployed position. Bone 300 is seen to have outer surface 301, and interior cancellous bone material 305 beneath outer cortex bone material 304. Bone bore hole 310 is seen to have cavity 312, proximal open end 314 and bottom 316. Cavity 312 of bone bore hole 310 is seen to be surrounded by bone surface 318. Next, as seen in FIG. 15, the surgeon moves the anchor 10 mounted to the distal end 224 of the elongated member 220 of insertion instrument 200 to a position within the cavity 312 of bone bore hole 310. If desired the anchor 10 can be deployed at any position within the bone bore hole 310 below the outer cortex layer 314. When the surgeon determines the desired depth within bone bore hole 310, the distal end 244 of support tube 240 is contacted with bone surface 318 surrounding open end 314 as seen in FIG. 16. The anchor up until this point remains in the undeployed configuration. Deployment of the anchor 10 in the bone bore hole 310 is illustrated in FIGS. 17–19. The deployment is initiated by exerting a force in the proximal direction upon the sutures 180. This causes actuation member 70 to slide proximally in outer member 20, thereby causing a camming action that pivots engagement members radially outward such that the proximal ends penetrate through the bone surface 318 and into the surrounding cancellous bone 305. The anchor is fully deployed when the maximum proximal movement has been achieved by the actuation member 70, as determined by the pin end 172 engaging the proximal end of pin slot 60. At full deployment a substantial section of each engagement member is deployed in the cancellous bone 305. After the anchor 10 has been completely deployed, the key projections 246 of instrument 200 are disengaged from the slots 31 of anchor 10 by pulling and/or twisting instrument 200, and the instrument 200 is then withdrawn from bore hole 310. As seen in FIG. 19, the anchor is fully deployed in the bore hole such that the anchor is in a fixed position and ready for the affixation of soft tissue to the surface 301 of the bone 300 with the sutures 160.

If desired, the anchor 10 may be removed from bore hole 310 after deployment of the engagement members 150. The distal end of the insertion device 200 is inserted into the bore hole 310 so that the key members engage the openings 31. Then, actuation member 70 is displaced distally by moving the instrument 200 distally to retrieve the engagement members 150 by causing the distal movement actuation member 70, causing the members 150 to disengage form the bone 305 and displace inwardly into slots 50 of outer member 20 and cavity 90 of actuation member 70. At this point the anchor device is not engaged with the surrounding material. The anchor 10 is withdrawn from the bone hole.

The bone bore holes into which a suture anchor of the present invention can be deployed will have a diameter and depth to provide for sufficiently effective anchoring and emplacement. These parameters will depend upon the diameter of the anchor in the undeployed and deployed configurations, as well as the length of the anchor. For example, if the anchor has an undeployed diameter of 2.3 mm, and a deployed overall diameter of 6.5 mm, the diameter of the bore hole can range from about 2.4 mm to about 2.9 mm mm. The length of the bore hole will typically be determined by the surgeon for a sufficiently effective depth, and will typically range from about 1 to about 2 times the length of the anchor.

The following examples are illustrative of the principles and practice of the present invention although not limited thereto.

EXAMPLE 1

A patient is prepared for arthroscopic surgery for a repair of a soft tissue injury in the patient's rotator cuff in the following manner. The patient is placed in a lateral position, or in a semi-sitting (beach chair) position, on a standard operating room table. After skin preparation and draping, full exposure of the coracoid process anteriorly and the entire scapula posteriorly is obtained. A standard posterior gleno-humeral arthroscopy portal is employed. An 18 gauge spinal needle is inserted toward the coracoid process anteriorly, in order to enter the gleno-humeral joint. The joint is inflated with sterile saline, and free outflow of fluid is confirmed as the inflating syringe is removed. Prior to making all portal incisions, the skin and subcutaneous tissue are infiltrated with 1% Lidocaine with Epinephrine, in order to reduce bleeding from the portals. The arthroscope cannula is inserted in the same direction as the spinal needle into the joint and free outflow of fluid is confirmed. Accessory portals may be inserted according to the preference of the surgeon. An initial diagnostic arthroscopy is conducted in order to identify the thickness and size of the tear. Through the lateral portal the edges of the cuff tear are debrided back to healthy tissue using an arthroscopic shaver. The bony bed is prepared on the greater tuberosity by roughening the cortical surface with a 5.5 mm burr to obtain punctuate bleeding and aid in the biologic reattachment of rotator cuff to bone. A drill is inserted through the suture punch cannula and used to pre-drill anchor insertion points on the greater tuberosity. The pre-drilled holes are typically 2.4 mm to 2.7 mm in diameter, and approximately 15 mm deep, depending on the dimensions of the preferred anchor and the nature of the bone. The suture anchors 10 of the present invention is inserted through the cannula and into the drill hole on the greater tuberosity. The engagement members 150 are deployed by pulling on the sutures 180 with a force of 2–10 lbs., while maintaining pressure on the inserter to maintain the position of the suture anchor in the drilled hole. The inserter is then withdrawn with a force of 2–10 lbs. to separate the suture anchor from the inserter shaft. Fixation is confirmed by tugging on the sutures with a force of 2–10 lbs. After the engagement members have been deployed in the bone surrounding the drilled hole, and the anchor is in a secured immobile position, the surgeon completes the surgical procedure for each anchor 10 by passing the two suture limbs of suture 180 through the supraspinatus tendon approximately 5 mm apart. A grasper is used through the lateral portal to pull the cuff tendon laterally onto the tuberosity in preparation for knot tying. A knot pusher is used to push appropriate knots down onto the tendon while maintaining lateral tension with the grasper. The two limbs of the suture 180 are cut with a suture cutter to complete the procedure. The tension of the suture maintains the soft tissue against the surface of the bone. The tension is maintained by the suture anchor 10, which is in a fixed position in the bore hole as a result of the deployment of the engagement members.

EXAMPLE 2

A second patient undergoes a similar surgical procedure to that described in Example 1. During the procedure, and after emplacement and engagement of suture anchor 10 in the drilled blind bore hole, it is necessary to remove the deployed anchor 10. The surgeon removes anchor 10 in the following manner. The insertion device 200 is positioned adjacent to the proximal end of the suture anchor 10, in alignment with axis of the device. The insertion device 200 is reattached to the anchor by pressing the distal tip of the inserter 200 onto the proximal end of the suture anchor 10 in openings 31. Continued insertion pressure is applied so that as the suture anchor 10 moves deeper into the drilled hole, the engagement members 150 retract into the slots 50 of outer member 20 and into cavity 90 of actuation member 70 of the suture anchor 10. The suture anchor 10 is then removed from the drill hole by removing the inserter/anchor assembly through the cannula.

An alternate embodiment of a suture anchor of the present invention is seen in FIGS. 20–23. The anchor 400 is seen to be similar in structure and operation to anchor 10. However, anchor 400 is seen to have a second set of engagement members 490 distal to the first proximal set of members 490, and rotated 90 degrees about the longitudinal axis 401 from the first proximal set. The anchor 400 is seen to have outer member 410 and actuation member 460. The outer member 410 is seen to have two pairs of engagement member slots 430 for the engagement members 490. The outer member 410 is seen to have pin slots 440 for the ends 487 of pin 485. The actuation member 460 has cavities (not shown) for mounting the engagement members 490 and for receiving pin 485. Member 460 is seen to have suture mounting hole 470 therethrough for receiving suture 180. The additional engagement members 490 may assist in providing additional pull-out strength. The anchor 400 is mounted to an insertion instrument 200 and deployed in a manner substantially similar to anchor 10.

Figure 24:
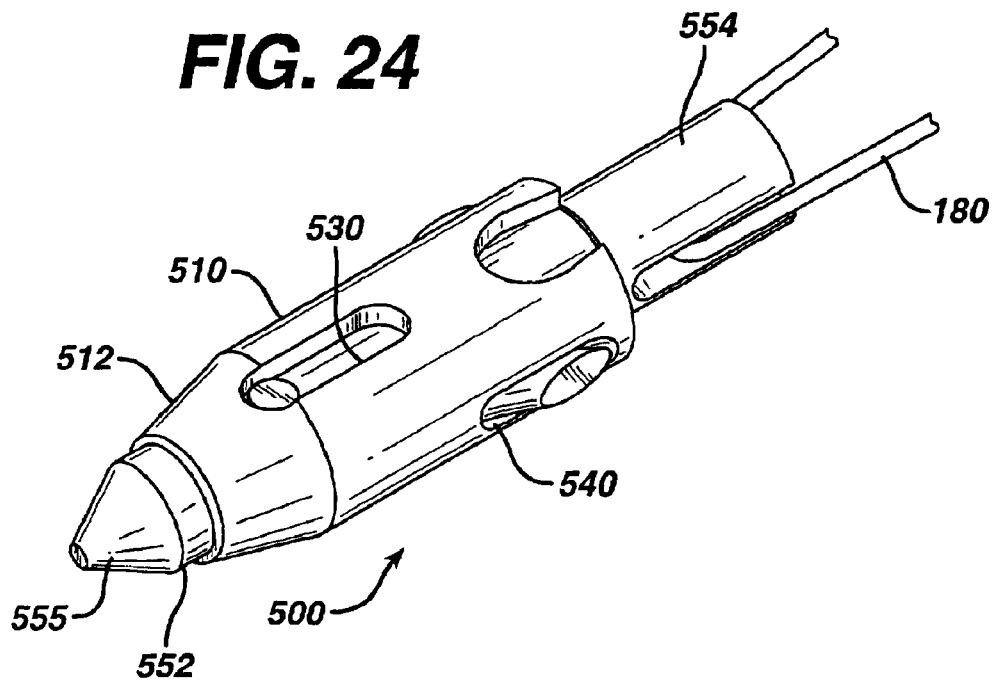
FIG. 24 is an alternate embodiment of a suture anchor of the present invention wherein the distal end of the outer member is open, and the distal end of the actuation member is conically shaped and extends through the distal open end of the outer member; the anchor is in the undeployed position.
Figure 25:
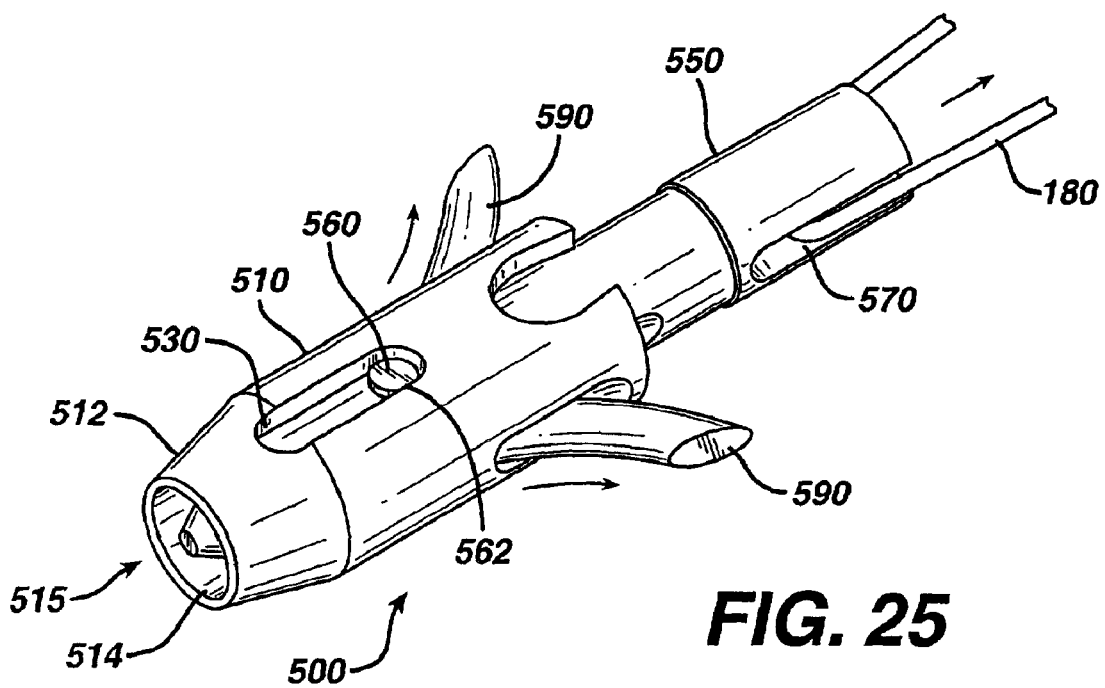
FIG. 25 illustrates the anchor of FIG. 24 in the deployed position.
Figure 26:
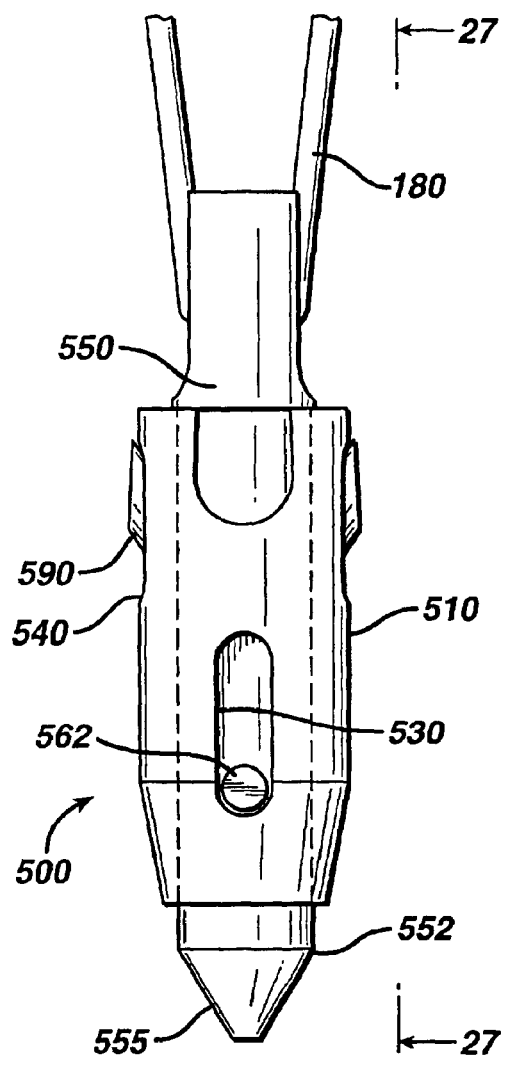
FIG. 26 is a side view of the anchor of FIG. 24 illustrating the engagement members and the pin members in then undeployed position, wherein the distal end of the actuation member extends through and out of the distal opening of the outer member.
Figure 27:
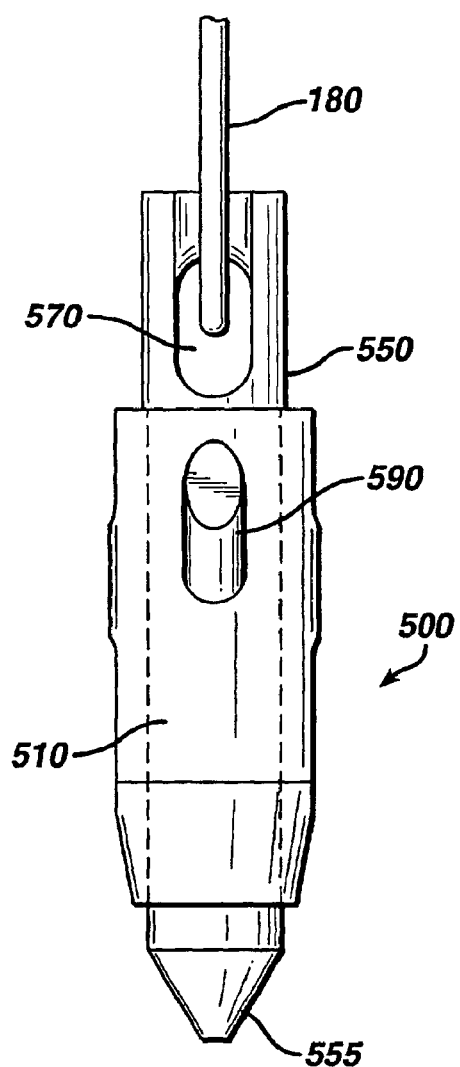
FIG. 27 is a side view of the anchor of FIG. 26 rotated 90 degrees about the longitudinal axis.

An additional alternative embodiment of a suture anchor of the present invention is seen in FIGS. 24–27. The anchor 500 is similar to anchor 10. In this embodiment, however, the distal end 512 of the outer member 510 has an opening 514. Outer member 510 is seen to be a tubular member having a passage or lumen 515 therethrough. The distal end 512 is optionally tapered in a frustoconical fashion. The actuation member 550 is substantially similar to actuation member 70, however the distal end 552 of actuation member 550 is seen to have a distally extending nose member 555 having a preferably substantially conical shape. Actuation member is seen to have suture mounting opening 570 therethrough at the proximal end 554. The anchor 500 is seen to have engagement members 590 mounted to the actuation member 550 and extending into slots 540. The anchor 500 is also seen to have pin 560 having ends 562 extending into slots 530. When the anchor 500 is assembled by slidably mounting actuation member 550 in outer member 510, the distal end 552 and nose section 555 are seen to extend distally out through opening 514 in the undeployed position as seen in FIGS. 24, 26 and 27. When in the deployed position as seen in FIG. 25, the distal end 552 and nose 555 are retracted proximally through opening 514 and are substantially or completely contained within passage 515.

Although the suture anchors of the present invention are designed to be used for soft tissue repair by facilitating the affixation of soft tissue to bone, the anchors are not limited to this use. For example the anchors may be used in other types of surgical procedures including bladder neck suspensions procedures, and plastic surgery procedures such a brow lifts.

The novel suture anchors of the present invention have many advantages. In the anchors of the present invention, the arcs are positioned within the profile of the anchor body and mechanically secured with a pin. Since the arcs are not exposed, the user can control the deployment of the arcs after the anchor body is placed in bone. In addition, the profile of the device is reduced, and the procedures can be performed through smaller incisions or cannulas. The assembly of the device is simple. Also, the insertion and locking of the device is achieved with two distinct operations. First, the anchor is placed in bone at the desired location without engaging the device. Secondly, the arcs are deployed and locked into bone by applying tension to the suture. The design and operation of the anchors of the present invention also provides for the ability to withdraw the anchors after employment.

Although this invention has been shown and described with respect to detailed embodiments thereof, it will be understood by those skilled in the art that various changes in form and detail may be made without departing from the spirit and scope of the claimed invention.

We claim:

1. A suture anchor, comprising:
    an outer member having a proximal end, a distal end, an inner cavity, an outer surface, and an inner surface;
    a distal nose member extending from the distal end of the outer member;
    an opening in the proximal end of the outer member in communication with the inner cavity;
    a pair of engagement member slots in said outer member extending through the outer surface and in communication with the inner cavity, said slots having a proximal end and a distal end;
    an actuation member slidably mounted in the cavity of the outer member, the actuation member having a proximal end, a distal end, and an outer surface;
    a cavity in said actuation member;
    a pivot pin member mounted in the cavity of the actuation member, the pivot pin member having opposed ends and an outer surface;
    a pair of engagement members pivotally mounted in the cavity of the actuation member about the pivot pin member, each engagement member having a proximal end, a distal end, and an outer surface; and,
    a camming surface extending distally in each engagement member slot,
    wherein the actuation member is moveable from a first distal position partially within the cavity of the outer member wherein the engagement members are contained within the outer member, to a second proximal position partially within the cavity of the outer member wherein at least the proximal ends of the engagement members extend out through the engagement member slots of the outer member such that said engagement members may engage bone.

2. The anchor of claim 1 additionally comprising a suture mounting opening in the actuation member.

3. The anchor of claim 1 additionally comprising a surgical suture mounted thereto.

4. The anchor of claim 1 wherein the engagement members comprise an arcuate shape.

5. The suture anchor of claim 1 wherein the proximal ends of the engagement members comprise a piercing edge.

6. The suture anchor of claim 1 wherein the outer member additionally comprises a pair of pin receiving slots in communication with the inner cavity of the outer member, the slots having opposed sides and opposed ends.

7. The suture anchor of claim 6, wherein the opposed ends of the pivot pin member extend into and are contained within the pin recieving slots.

8. The suture anchor of claim 6, wherein the opposed ends of the pivot pin member are in frictional contact with the sides of the pin recieving slots.

9. The anchor of claim 1, wherein the engagement member slots comprise a camming surface extending from the proximal ends.

10. The anchor of claim 1, wherein the engagement members have an indentation in the distal ends, and a camming surface about the indentation.

11. The anchor of claim 1 additionally comprising a second set of engagement members mounted in the cavity of the actuation member and a second pair of engagement member slots in the outer member.

12. A method of affixing soft tissue to bone, the method comprising:
    providing a suture anchor, the suture anchor comprising:
        an outer member having a proximal end, a distal end, an inner cavity, an outer surface, and an inner surface;
        a distal nose member extending from the distal end of the outer member;
        an opening in the proximal end of the outer member in communication with the inner cavity;
        a pair of engagement member slots in said outer member extending through the outer surface and in communication with the inner cavity, said slots having a proximal end and a distal end;
        an actuation member slidably mounted in the cavity of the outer member, the actuation member having a proximal end, a distal end, and an outer surface;
        a cavity in said actuation member;
        a pivot pin member mounted in the cavity of the actuation member, the pivot pin member having opposed ends and an outer surface;
        a pair of engagement members pivotally mounted in the cavity of the actuation member about the pivot pin member, each engagement member having a proximal end, a distal end, and an outer surface;
        a camming surface extending distally in each engagement member slot; and,
        a surgical suture mounted to the actuation member,
        wherein the actuation member is moveable from a first distal position within the cavity of the outer member wherein the engagement members are contained within the outer member, to a second proximal position within the cavity of the outer member wherein at least the proximal ends of the engagement members extend out through the engagement member slots of the outer member such that said engagement members may engage bone;
    accessing a bone and drilling a hole into the bone;
    inserting the suture anchor into the hole in the bone and deploying the engagement members into bone surrounding the hole in the bone by pulling proximally on the sutures causing the actuation member to move proximally with respect to the outer member to the second proximal position; and,
    engaging soft tissue with the suture and approximating the soft tissue to the bone.

13. A suture anchor, comprising:
    an outer member having a proximal end, a distal end, an inner cavity, an outer surface, and an inner surface;
    an opening in the proximal end of the outer member, and an opening in the distal end of the outer member, wherein both openings are in communication with the inner cavity;
    a pair of engagement member slots in said outer member extending through the outer surface and in communication with the inner cavity, said slots having a proximal end and a distal end;
    an actuation member slidably mounted in the cavity of the outer member, the actuation member having a proximal end, a distal end, and an outer surface;

a distal nose member extending from the distal end of the actuation member;

a cavity in said actuation member;

a pivot pin member mounted in the cavity of the actuation member, the pivot pin member having opposed ends and an outer surface;

a pair of engagement members pivotally mounted in the cavity of the actuation member about the pivot pin member, each engagement member having a proximal end, a distal end, and an outer surface; and, a camming surface extending distally in each engagement slot, wherein the actuation member is moveable from a first distal position partially within the cavity of the outer member wherein the engagement members are contained within the outer member and the distal nose member of the actuation member extends out through the distal opening of the outer member, to a second proximal position partially within the cavity of the outer member wherein at least the proximal ends of the engagement members extend out through the engagement member slots of the outer member such that said engagement members may engage bone.

14. The anchor of claim 13 additionally comprising a suture mounting opening in the actuation member.

15. The anchor of claim 13 additionally comprising a surgical suture mounted thereto.

16. The anchor of claim 13 wherein the engagement members comprise an arcuate shape.

17. The suture anchor of claim 13 wherein the proximal ends of the engagement members comprise a piercing edge.

18. The suture anchor of claim 13 wherein the outer member additionally comprises a pair of pin receiving slots in communication with the inner cavity of the outer member, the slots having opposed sides and opposed ends.

19. The suture anchor of claim 18, wherein the opposed ends of the pin member extend into and are contained within the pin recieving slots.

20. The suture anchor of claim 19, wherein the opposed ends of the pin member are in frictional contact with the sides of the slots.

21. The anchor of claim 13, wherein the engagement member slots comprise a camming surface extending from the proximal ends.

22. The anchor of claim 13, wherein the engagement members have an indentation in the distal ends, and a camming surface about the indentation.

23. The anchor of claim 13 additionally comprising a second set of engagement members mounted in the cavity of the actuation member and a second pair of engagement member slots in the outer member.

* * * * *